United States Patent
Stillman

(10) Patent No.: US 11,779,667 B2
(45) Date of Patent: Oct. 10, 2023

(54) ULTRAVIOLET LED LIGHT SANITIZER AND DEVICES SANITIZED THEREBY

(71) Applicant: Richard I. Stillman, Mountain Lakes, NJ (US)

(72) Inventor: Richard I. Stillman, Mountain Lakes, NJ (US)

( * ) Notice: Subject to any disclaimer, the term of this patent is extended or adjusted under 35 U.S.C. 154(b) by 382 days.

(21) Appl. No.: 16/985,625

(22) Filed: Aug. 5, 2020

(65) Prior Publication Data
US 2022/0040343 A1 Feb. 10, 2022

(51) Int. Cl.
*A61L 2/10* (2006.01)
*A47J 43/28* (2006.01)
*A41D 19/01* (2006.01)

(52) U.S. Cl.
CPC .............. *A61L 2/10* (2013.01); *A41D 19/01* (2013.01); *A47J 43/283* (2013.01); *A61L 2202/11* (2013.01); *A61L 2202/122* (2013.01)

(58) Field of Classification Search
CPC .. A61L 2/10; A61L 2202/11; A61L 2202/122; A41D 19/01; A41D 13/087; A47J 43/283
See application file for complete search history.

(56) References Cited

U.S. PATENT DOCUMENTS

| | | | |
|---|---|---|---|
| 2008/0199354 A1* | 8/2008 | Gordon | A61L 2/10 422/186.3 |
| 2013/0025016 A1* | 1/2013 | Koffi | G06F 3/044 2/21 |
| 2014/0158910 A1* | 6/2014 | Fletcher | A61L 2/10 250/455.11 |
| 2017/0360977 A1* | 12/2017 | Stibich | A61L 2/20 |
| 2019/0298871 A1* | 10/2019 | Dobrinsky | A61L 2/10 |

FOREIGN PATENT DOCUMENTS

CN 110180002 A * 8/2019 ............. A61L 2/10

OTHER PUBLICATIONS

English translation of CN110180002 (Year: 2019).*

* cited by examiner

*Primary Examiner* — Regina M Yoo
(74) *Attorney, Agent, or Firm* — H. Jay Spiegel

(57) ABSTRACT

A portable sanitizing system for rapidly dispensing reusable finger coverings for handling contaminated surfaces in a sanitary fashion. A battery operated ultraviolet LED system sanitizes finger coverings which are customized for use with the sanitizing device. The sanitary finger coverings can be rapidly applied to the user's hand without contamination, using a single hand. Repeated sanitization and utilization are similarly rapid and easy. The sanitizer can be carried by the user or attached to their uniform. The reusable finger covers can be custom fit to a variety of hand sizes and are optimally designed to work with the sanitizing device. The implement aids in grasping surfaces securely without touching the surface with the user's bare fingers.

9 Claims, 16 Drawing Sheets

ULTRAVIOLET LED LIGHT SANITIZER AND DEVICES SANITIZED THEREBY

BACKGROUND OF THE INVENTION

The present invention relates to an ultraviolet LED light sanitizer for sanitizing various devices including finger covers such as, for example, gloves. The field of endeavor of the present invention includes infection control and devices which prevent transmission of infection, such as sterilizers and gloves.

The COVID-19 pandemic has created heightened awareness about the surfaces we contact with our bare hands. It has been shown that viruses, as well other infectious microbial agents involved in epidemics, may remain viable and transmissible on many surfaces for a significant period of time. Once in contact with a contaminated surface, the hand may become a vector of microbial transmission by touching other surfaces, other people, or one's own face.

Many occupations require performing tasks which involve frequent contact with contaminated surfaces, such as waiters, mail handlers and other delivery persons, cashiers, secretaries, bank tellers, packagers at distribution centers, and school teachers to name a few. Performing these tasks using a "no touch" technique is an evolving goal, which must be balanced against the inconvenience, expense and environmental impact of disposable gloves.

This problem is of particular concern to the restaurant industry, since waiters generally serve plates of food using their bare hands. In most cases, the thumb grasps the top surface of the plate containing food while the other four fingers support the undersurface of the plate. See FIG. 1. This creates a potential source of transmission of infectious agents from the waiter's fingers, particularly the thumb, to the consumer of the food on the plate. Additionally, removing a used plate in this fashion after a meal potentially exposes the waiter's fingers to the patron's oral secretions left on the plate. This cycle of serving and removing plates is repeated over and over again, from customer to customer, amplifying the risk of transmission of disease.

The National Outbreak Reporting System (NORS) at the Center for Disease Control (CDC) has documented over 46,000 outbreaks of food-born illnesses since 1998, involving well over one million individuals, causing 31,000 hospitalizations and 1,500 deaths. Many orders of magnitude more undocumented outbreaks and individual episodes of food-borne illnesses have likely occurred. A large variety of microbial species, both bacterial and viral, have been identified as the infectious agents in these outbreaks. Food handlers, including servers, have been implicated in a significant proportion of these outbreaks. Often, a food-worker may be contagious and shed infectious microbes onto their own fingertips several days before becoming symptomatic. This makes identification and isolation of the infectious individual difficult. While the current Coronavirus pandemic has become the primary focus, many other pathogens are also problematic. Most recently, a single asymptomatic food handler with Hepatitis A was implicated in the infection of 17 persons, including one death, at The Mendham Country Club in New Jersey in 2019.

The Centers for Disease Control (CDC) and health departments across the country have promulgated guidelines and recommendations addressing this problem. Central to these recommendations is regular and meticulous hand washing as well as usage of gloves when food handlers are in direct contact with food or serving plates. However, both of these interventions have been documented to have low compliance rates. Additionally, studies have shown that gloves quickly become contaminated when worn for more than a brief period of time. Contamination may unknowingly occur when the user inadvertently touches their nose, mouth or any other contaminated surface, such as a used food plate.

Given the fear associated with the current pandemic, the revitalization of the restaurant industry will largely depend upon the public's confidence in the food they are served. Many other occupations would also benefit from a device which facilitates a "No-Touch" method of handling potentially contaminated items. This includes any item which is handled by one person and ultimately handled by another person, such as the many items shipped by mail, school homework assignments, etc.

The present invention is intended to solve this problem by providing a novel device, method and system for rapidly sanitizing and applying reusable finger covers. The covers may be utilized by waiters for serving and handling dishes, glasses, and other food containing surfaces. Many other jobs, which involve repeated handling of items touched by others, such as bank tellers, cashiers, letter carriers, school teachers, personnel who pack items in boxes for shipping, etc., could utilize the present sanitizing system. Other small objects, such as forks and knives, pens, credit cards, money, salt and pepper shakers can be sanitized by the device as well.

The following prior art is known to Applicant:

U.S. Published Application No. US 2010/0088794 A1 to Oradini, Sr. (Oradini) discloses disposable sanitary finger covers, a dispenser for the covers and a method for applying the covers. The covers described are designed to protect the user's fingers FROM contact with contaminated surfaces. The present invention prevents transmission of microbes from the user's fingers TO a surface. The Oradini device is designed for multiple untrained users in public places like bathrooms and is mounted permanently in such locations. Repeated improper use in this way amplifies the risk of dispensing a contaminated cover. Additionally, the annular membrane described by Oradini, designed to prevent dispensing multiple tubular covers, is a potential source for contamination upon withdrawal from the device, since it may come in contact with the fingers of multiple untrained individuals. There is also a risk of contaminating the stacked covers within the dispenser by aerosolized particles, since it is repeatedly accessed. As such, even clean, boxed, disposable gloves have been documented to become contaminated over time in various environments, such as operating suites, kitchens, bathrooms and restaurants. There is no known method of maintaining a sanitized cover within the device. The inability to re-sanitize or reuse the covers represents the biggest disadvantage and difference from the present invention.

By contrast, the novel design of the present invention finger cover system sanitizes the covers immediately prior to use, providing freshly sanitized covers. The device can be utilized, cared for and cleaned by a single individual who is skilled in its use. It is portable and may be easily carried by the user to different locations of use, such as at a table at a restaurant. Most importantly, the finger covers are reusable and may be sanitized within the device many times before disposal.

The tubular shape, size and appearance of Oradini's covers are overly complicated with respect to the present invention. The Oradini covers may inhibit facile usage of the fingers while serving food and possibly decrease grip on a surface, such as a plate. The novel design of the finger covers in the present invention improves adhesion to the surface of the plate, while also protecting the user from a potentially hot surface. Finally, the Oradini finger covers require either an adhesive or complex surface texture in order to dispense the covers individually. The present device requires no adhesive, attaching to the finger in some embodiments, using a novel custom fit design, using heat-moldable plastic. In other embodiments, a mechanism connecting each finger element is provided, promoting retention on the finger. Additionally, the covers are easily applied without need for textured interior and exterior surfaces as in the Oradini device.

U.S. Pat. No. 9,723,879 to Delgrosso also describes tubular finger sheaths, which maintain their sanitary state by impregnation with antimicrobial agents. Such agents have the disadvantage of creating an unwanted exposure of the food surface to the antimicrobials, potentially causing an allergic reaction. There is an unnecessary expense attendant to antimicrobial application. There is also a negative environmental impact upon disposal, potentially causing multiple drug resistant microbial strains at the site of disposal, such as at a landfill.

U.S. Published Application No. US 2008/0000011 A1 to Ayala discloses a sanitary finger cover made from flexible material, preferably plastic, in the shape of a pocket. Neither a method of dispensing the cover nor any means of maintaining the cover sanitary is disclosed.

U.S. Published Application No. US 2013/0025016 A1 to Koffi et al. (Koffi) discloses fingertip covers made from various materials, which allow control of touch screen electronics. The primary purpose is to prevent contamination of the user's fingers. The tips adhere to each finger with adhesive and require a backing strip to be removed with a second hand. No sanitary aspect is disclosed.

The prior art discussed above fails to describe devices or methods of dispensing sanitary finger covers which meet the requirements of being sanitized on demand, are inexpensive, inconspicuous, portable, rapidly applied with one hand, using a non-slip material, custom fitting, which provides thermal protection and which may be reusable or disposable and biodegradable.

SUMMARY OF THE INVENTION

The present invention relates to an ultraviolet LED light sanitizer for sanitizing finger covers and other devices. The present invention includes the following interrelated objects, aspects and features:

(1) The first component of the invention is the sanitizing device, which is portable, lightweight and intended to be carried by the user in an unobtrusive fashion. The device is preferably rectangular in shape and resembles a miniature, top-loading bread toaster. It weighs less than a pound and is approximately 3" high×5" length×2" wide. Various size models of the device are provided depending on the application. It may be attached to the user's belt or uniform with a belt clip or other attachable means, such as hook and pile fastening means sold under the registered trademark VELCRO®. It may function as a freestanding, table-top device if desired.

(2) The sanitizing mechanism within the device is an array of ultraviolet LEDs, which emit wavelengths of light between 250 and 300 microns. These ultraviolet LEDs emit sufficient intensity and duration of ultraviolet light to effectively disinfect the item to be sanitized. Different wavelengths of ultraviolet light are provided depending on the application. Ultraviolet LED systems are commonly available from multiple vendors as stock items, as are their constant-current regulators. Both are readily customizable and in common use in other applications. The power source is a consumer grade disposable or rechargeable battery.

(3) The second novel component of the invention is the "No Touch Tool" (NTT). The NTT consists of reusable thumb and finger coverings. These coverings are designed to cover the distal phalanx of the thumb and fingers. Multiple embodiments of the finger covers are disclosed. In some embodiments, the distal two phalanxes are covered, separated by a flexible portion, allowing movement at the distal joint of the finger. In one embodiment, the finger component covers multiple fingers together, in a single covering resembling a "mitt." In another embodiment, the finger component provides independent finger covers for each finger. The coverings are made from materials selected from the group consisting of cloth, fabric, pulp cardboard, paper, wood, metal, plastic, or composite. The material must remain functional after multiple exposures to ultraviolet light. The material may be recyclable, biodegradable, sterilizable, reusable and/or disposable. The coverings are lightweight, nonabsorbent and inexpensive to manufacture. In some embodiments, the coverings are made from heat moldable plastic, allowing the user to form fit the covering to their individual finger shapes and sizes.

(4) In some embodiments, the thumb and finger components of the NTT are separate individual components, allowing for total independent movement between the thumb and finger components. In other embodiments, the thumb and finger components are a single unit, attached by any attachable means which allows some degree of independent movement between the thumb and finger components. This embodiment may resemble and function as a glove, covering not only the proximal phalanxes of the digits but also include the distal part of the hand. This attachable means may be a simple attachment, such as a piece of material, string or wire. A mechanical attachment similar to a "Bobbie Pin" or a tong is also disclosed. This consists of two arms attached by a flexible junction which allows reversible apposition of the thumb and finger components. The ability to attach the thumb and finger components serves to facilitate applying and removing the components using the single hand. The attachment of the thumb and finger components also improves overall stability and function of the NTT, as well as preventing inadvertent release of an individual finger or thumb component. The attachment of the components also serves to coordinate movement between the components in some applications. In other embodiments, the attachable means includes a surface, which inserts into a slot in the thumb and finger components, of predetermined size to receive the surface. The surface functions to reversibly attach the thumb and finger components while providing additional rigidity, durability and thermal insulation, for use with hot or cold objects.

(5) In a first embodiment, the housing of the sanitizing device has two side-by-side openings on the top surface. These openings are of predetermined size and shape to optimally fit and receive the thumb and finger components of the "No Touch Tool" (NTT). The novel design of the "NTT" functions optimally with this embodiment. The thumb component of the NTT is inserted into the first opening, which is of predetermined size to precisely fit this component. The finger component is inserted into the second opening, which is of predetermined size to precisely fit the component. In embodiments in which the finger component contains individual components for each finger, there are openings for each individual finger component. The two components are separated by a dividing center wall, which contains a plurality of ultraviolet LEDs on both sides. Each of the two grasping, contact surfaces of the NTT face centrally, toward the dividing center wall, between the openings. This orientation places the contact surfaces of the NTT in direct apposition to the ultraviolet LEDs embedded within the center wall of the device. All embodiments of the NTT achieve optimal function with the sanitizing device, whether as attached or independent thumb and finger components.

(6) The center wall is a removable module, which can be adjustably attached in various positions and locations on the main housing. The module is connected to the main housing using an attachable means, such as a snap, magnet or adhesive connection such as a hook and pile fastening means sold under the registered trademark VELCRO®. In some embodiments, the modular side walls are also detachable and may be adjustably reattached in different locations on the main housing in a similar fashion to the center wall module. This allows the user to adjust and optimize the location of the ultraviolet LEDs around the items to be sanitized. This adjustability also allows items of different shapes and sizes to be optimally placed in the sanitizing device. This novel design increases the overall efficacy and efficiency of sanitization by decreasing the distance from the inserted item to the sterilizing light source. The design also decreases the exposure time and the intensity of light required to sanitize effectively. The adjustable, modular wall design also allows items of varying shapes and sizes to be quickly inserted and removed. The modular design also allows greater access to all surfaces of the device for cleaning purposes.

(7) The electrical contact between the modular walls and the source of power within the main housing may be any electrical attachment means, such as a nine-volt battery snap connector, mini-jack, RCA or USB type connector. In some embodiments, both the center wall and side walls contain their own battery power supply. This allows the individual modular walls to remain active while removed from the main unit, which may advantageous in some applications. This also avoids the need for separate electrical contacts between the wall modules and the main housing.

(8) While the device is designed to optimally function using the NTT in all its embodiments, other types of items and implements may be used with the sanitizing device. The size of the top openings is adjustable due to the modular, movable wall design. This accommodates multiple different sized and shaped implements for insertion. For example, the user may insert the functional end of an implement, such as tongs into the device for sanitization. The handle of the implement remains outside the device for easy removal using a single hand. Insertion of the implement or NTT triggers operation of the ultraviolet LEDs using any automatic switch mechanism, such as an electric eye. Operation may also be triggered manually with an on/off switch. The implement, or NTT, is then exposed to sufficient ultraviolet light intensity and duration to achieve effective sanitization. The coronavirus responsible for Covid-19 has been shown to sensitive to ultraviolet light, as have many other infectious agents.

(9) Once sanitized within the device, the user removes the implement by grasping the non-sanitized handle, which extends outside the device. The user then slides the now sanitized functional end of the implement out of the sterilizer through the sanitary side openings. This process can be achieved using a single hand. This novel method and design avoids recontamination of the implement upon removal.

(10) The novel design of the NTT allows the user to insert the NTT directly into openings on the top surface of the sterilizer, which are sized to optimally receive them. A rim or tab 57, 59 (FIG. 2) on the open ends of the thumb and finger components serves to limit the depth of insertion into the sterilizer. This is achieved by the rim or tab reversibly snapping into a recess in the sterilizer opening, of predetermined size to receive the rim or tab, during insertion. This provides enough resistance and retention of the NTT to allow the user to remove their fingers while leaving the NTT within the sterilizing device. The user removes the sanitized NTT by simply inserting their thumb and fingers into the respective thumb and finger component openings of the NTT and sliding the NTT out of the sanitary side openings of the sterilizer. In one embodiment, optimized for use with the NTT, the side wall modules of the sterilizer tilt outwards on hinges, at completion of sanitization, for removal of the NTT. This is effectuated by the user inserting their thumb and fingers into their respective components of the NTT and spreading the thumb and finger components outwards against the side walls, away from the center wall. A rubber band mechanism, or other flexible mechanism, holding the side wall components in the upright position, expands outward as the hand opens. This allows removal of the NTT upward, in the opposite direction of insertion. This method also prevents recontamination of the contact surfaces of the NTT upon removal.

(11) The sanitizing device is lightweight and can be fashioned from a variety of inexpensive materials, such as plastic, metal or composite materials. In one embodiment, the device is attached to the user's belt buckle with a clip or other attachable means, allowing hands-free operation while the user is performing other tasks. The low electrical power requirement of LEDs allows the device to be operated with consumer grade rechargeable or disposable batteries.

(12) Summarizing, several novel features and advantages are apparent from the detailed description of the embodiments of the present invention in the specific description of the preferred embodiments. These include providing a freshly sanitized means for handling plated food and beverages without the server ever touching the food containing surfaces. Additionally, a variety of commonly used table side items, such as salt and pepper shakers, utensils, etc., may be sanitized at the table side, as needed. Many non-food handling applications, which require repeated touching of potentially contaminated surfaces, such as mail handlers, cashiers, bank tellers, packers of goods for shipping, school teachers, etc., may benefit from using the device.

(13) The sanitizing device may be fashioned from a variety of lightweight, inexpensive materials. The ultraviolet LEDs are available off-the-shelf from a large number of manufacturers and in common use in other devices which utilize LEDs. Constant-current regulators are required to efficiently manage power consumption of the LEDs and are also available as stock items, integrated into the LED assembly.

Accordingly, it is a first object of the present inventions to provide an ultra-violet LED light sanitizer and devices sanitized thereby and used for sanitizing finger covers and implements used by waiters for handling food containing surfaces, such as dishes and glasses. Many other applications, involving frequent handling of non-sanitary surfaces, may utilize the described system.

It is a further object of the present invention to provide such a device which can quickly and easily dispense sanitized implements, such as the NTT, with little or no waiting time.

It is a still further object of the present invention to provide a lightweight, portable sanitizing device which can be carried hands-free by the user.

It is a further object of the present invention to provide sanitized implements, such as the NTT, immediately at the time of use, on demand, to avoid contamination between sanitizations.

It is a still further object of the present invention to provide a renewable, sanitary means of handling food containing surfaces, as well as other contaminated surfaces, as an alternative to disposable gloves.

It is a further object of the invention to provide custom fit finger covers, which can be rapidly applied to the fingers, inserted into the sanitizing device, and rapidly reapplied to the fingers during removal from the device.

It is a still further object of the present invention to allow removal of the sanitized implements from the device, using a single hand, in such a fashion as to avoid recontamination of the implement or NTT.

It is a further object of the present invention to provide a modular design to accommodate different sized items for sanitization and to facilitate access for cleaning.

It is a still further object of the modular design of the present invention to provide an adjustable means for locating and orienting the ultraviolet LEDs within the device to optimize effective sanitization of all surfaces of the inserted implement.

It is a still further object of the present invention to operate at battery level voltages. The low power consumption of LEDs, as well as the novel adjustable walls, avoid the need for a high voltage, ozone-generating ultraviolet light source, as with other sterilizers.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
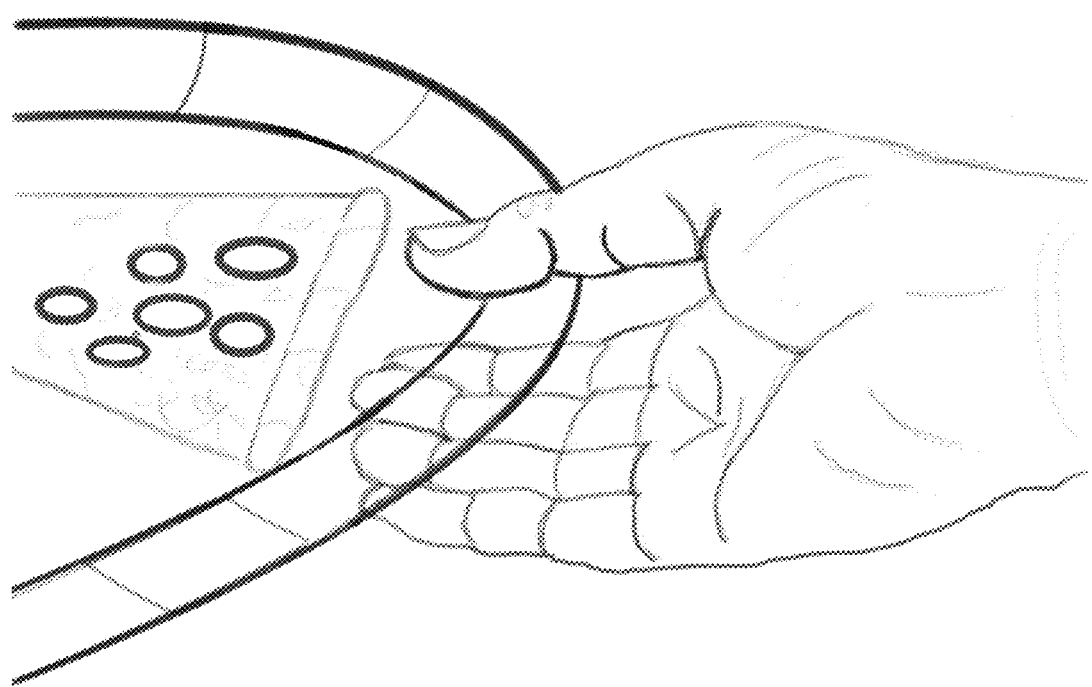
FIG. 1 shows a the typical position of a bare hand serving a plate of food. The thumb stabilizes the top surface of the plate, which contains food. The remaining fingers support the undersurface of the plate.
Figure 2:
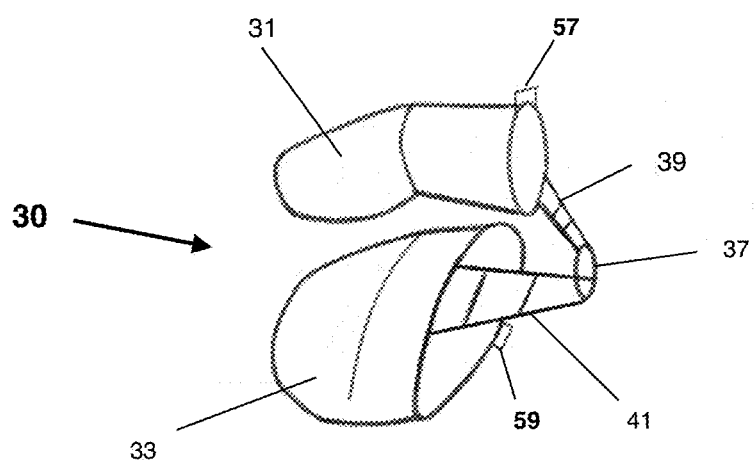
FIG. 2 shows one embodiment of the "No Touch Tool" (NTT) consisting of a thumb component attached to a finger component by a fulcrum mechanism. In this embodiment, the finger component encloses all fingers, in the shape of a mitt.
Figure 3:
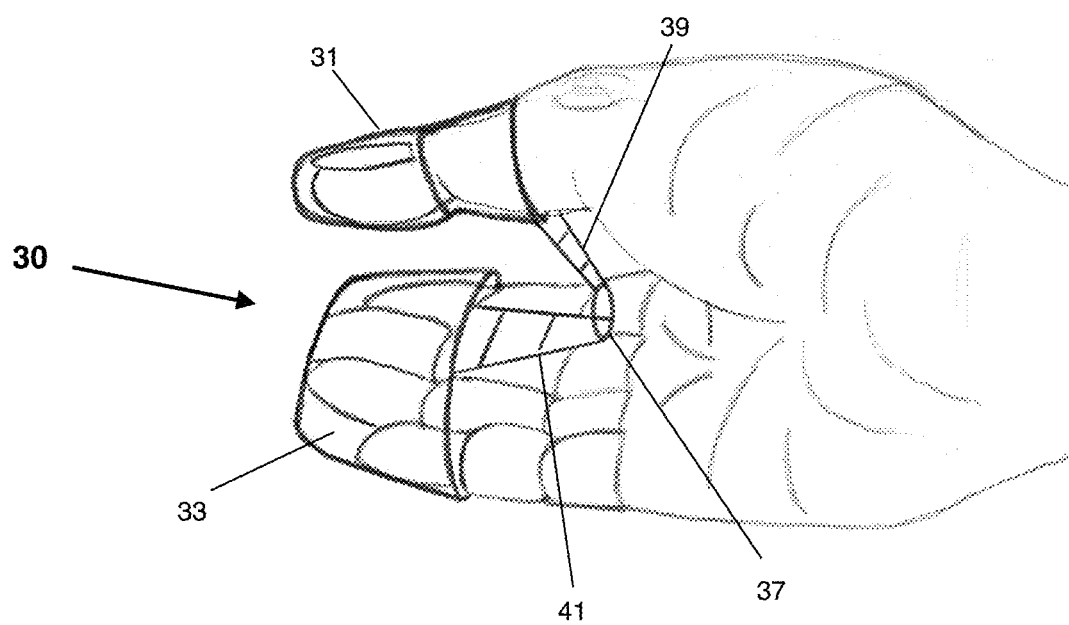
FIG. 3 shows the NTT attached to the user's hand.
Figure 4:
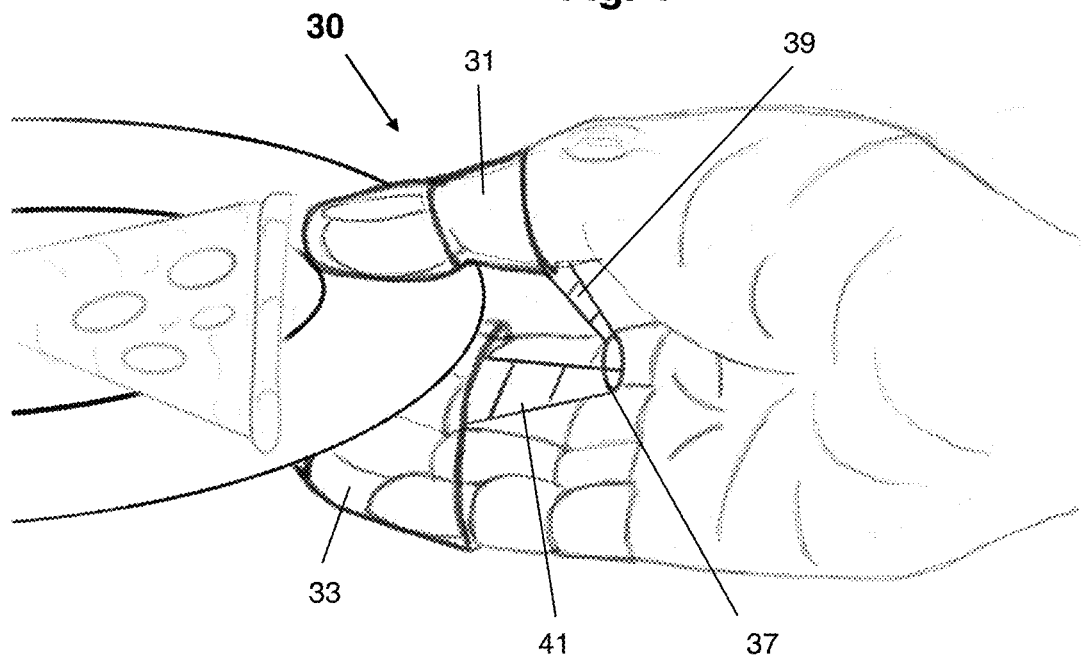
FIG. 4 shows the user serving a plate of food using the sanitized NTT.
Figure 7:
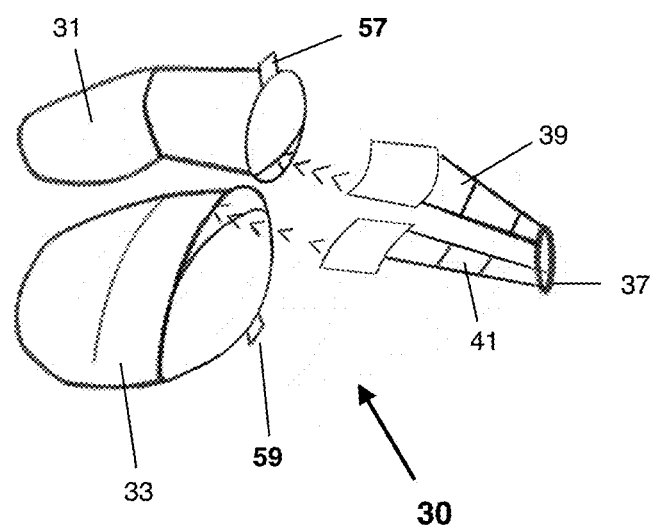
FIG. 7 shows an exploded perspective view of the NTT showing the optional insertable fulcrum mechanism for attaching the thumb and finger components. The insertable pads on the aims of the fulcrum mechanism provide support and insulation for handling hot surfaces. The thumb and finger components may be used independently, without the attachable fulcrum mechanism.
Figure 8:
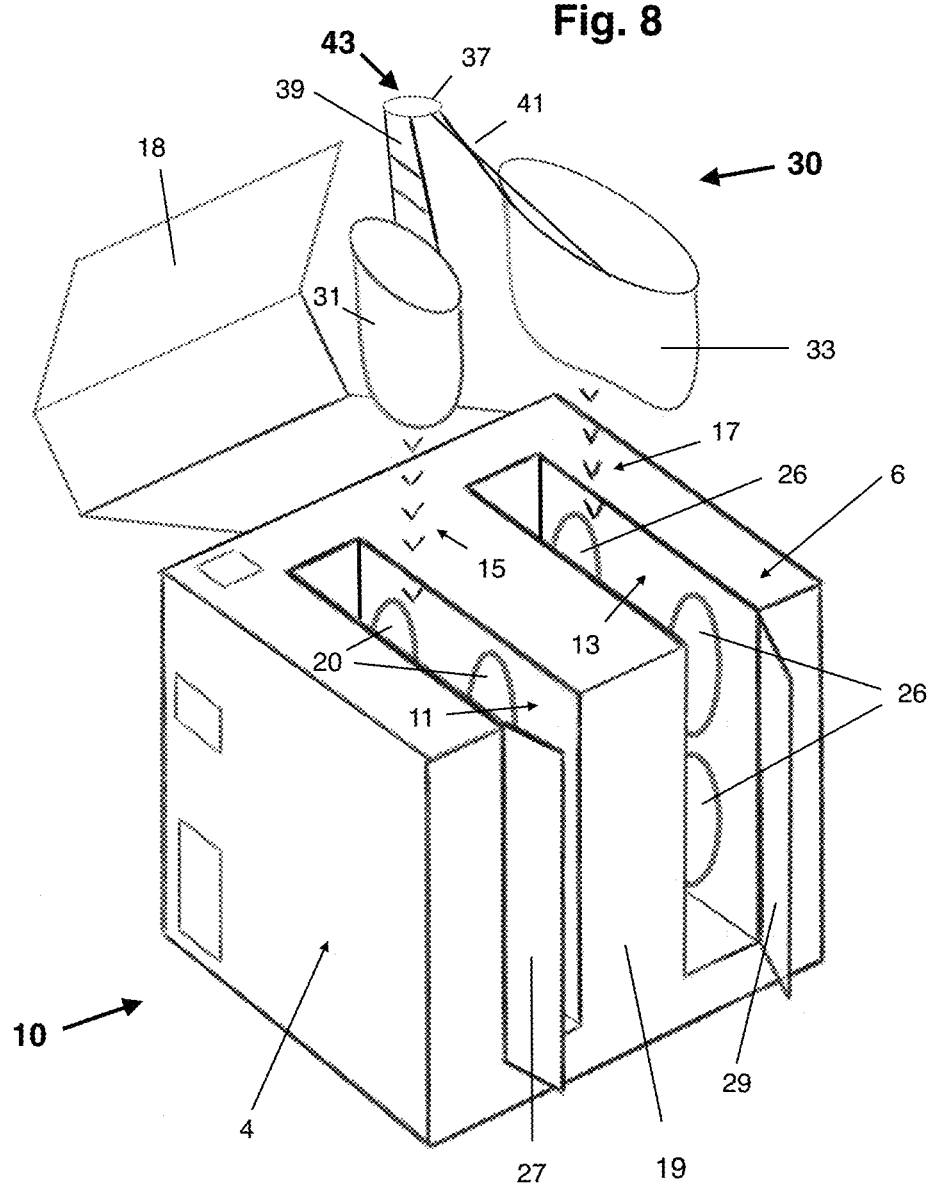
FIG. 8 shows a side front perspective view of the sanitizing device constructed in accordance with the invention, showing the "No Touch Tool" or NTT, being inserted into the two horizontal top openings, in the direction of the downward pointing arrowheads. The internal surfaces of the sanitizing device are lined with ultraviolet LEDs, indicated by oval shapes.
Figure 9:
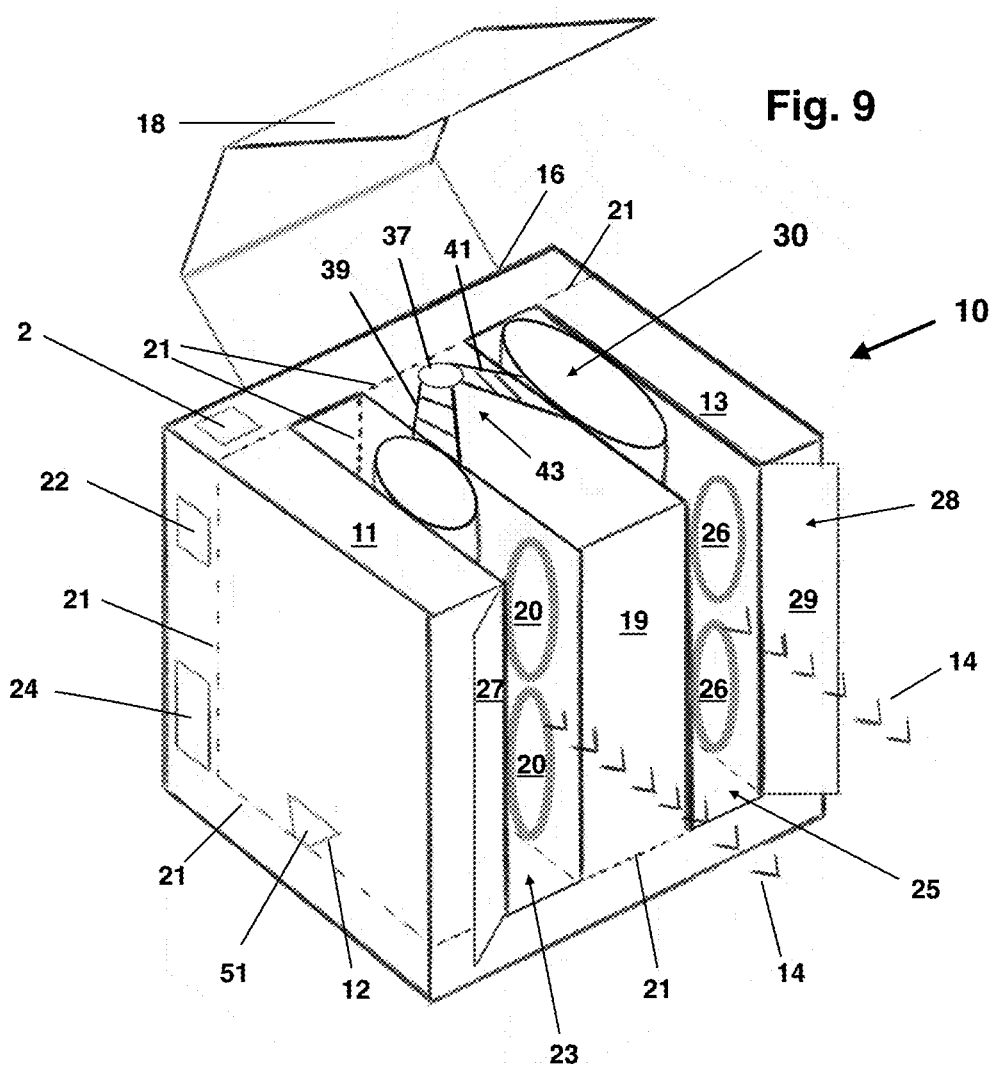
FIG. 9 shows the device of FIG. 8 with the NTT inserted.

With reference to FIGS. 8-9, a first embodiment of the sanitizing device is shown, generally designated by the reference numeral 10. The NTT 30 is shown being inserted into the two top horizontal openings 11, 13 of the sanitizing device. See also FIGS. 2-4. The NTT 30 is inserted in the downward direction, as indicated by the downward pointing arrowheads 15, 17. The thumb component 31 of the NTT 30 is shown being inserted into the left top horizontal opening 11. The manner of assembly of the NTT 30 is shown in FIG. 7. The finger component 33 of the NTT 30 is shown being inserted into the right top horizontal opening 13 of the device 10. The openings or sub-chambers 11 and 13 are defined by walls 4, 6 and 19. The two components of the NTT 30 are separated by the center wall 19 of the device. The contact surfaces of the thumb and finger components of the NTT are in direct apposition to the ultraviolet LEDs 20 on the center wall module. The center wall or partition 19 is a removable module, as indicated by dotted lines 21 in FIG. 9 at the points of detachment. The vertical side exit openings 23, 25, through which the NTT 30 is removed, are covered by hinged door panels 27, 29. These door panels 27, 29 are hinged to open outward in the direction of removal of the NTT 30. Therefore, during removal, the sanitized NTT 30 only comes in contact with the inner sanitary surface, for example, 28 of the door panel 29 of the exiting door panel. This inner surface 28 is continuously exposed to the ultraviolet LEDs and at all times remains sanitary. This novel design prevents recontamination of the NTT 30 during removal from the sanitizing device.

The internal surfaces of the walls 4, 6 of the sanitizing device 10 are shown lined with a plurality of ultraviolet LEDs, indicated by ovals 26. The center wall 19 is lined with ultraviolet LEDs 20 as well. The ultraviolet LEDs 20, 26 emit wavelengths of light between 250-300 microns, which is effective at sanitizing multiple infectious microbial agents. The ultraviolet LEDs 20, 26 are powered by rechargeable batteries, which are housed in compartment 24, FIG. 9. A constant-current regulator 22, shown adjacent to the battery compartment, controls operation of the ultraviolet LEDs 20, 26. In some embodiments, the constant-current regulator 22 is an integrated component of the LED assembly. Multiple manufacturers provide an ultraviolet LED with an integrated constant-current regulator as a stock item. An on/off switch 2 is shown on the top panel of the device.

The top lid 18 of the device is shown in open position. The user manually swivels the top lid into closed position during the sanitization cycle about hinge 16. This prevents exposure of ultraviolet light outside the device during operation. The lid 18 is sized and shaped to accommodate the protruding handle 43 of the inserted NTT or other implement, such as a pair of tongs.

Figure 5:
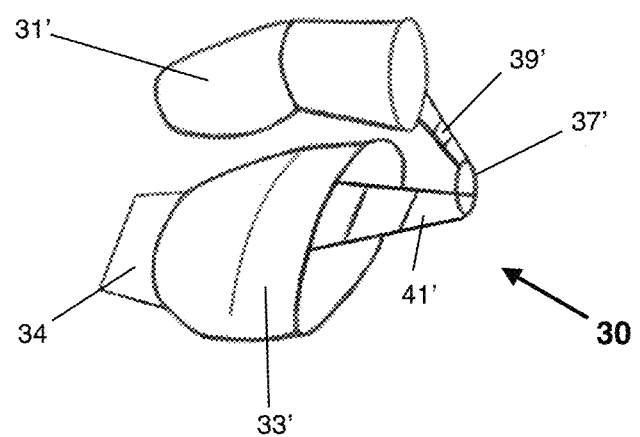
FIG. 5 shows another embodiment of the NTT with a flat rigid front extension. The extension facilitates sliding the finger component under a flat surface, such as a dinner plate.

FIG. 9 shows the device 10 of FIG. 8 with the NTT 30 inserted. The functional end of the NTT, which includes the thumb 31 and finger 33 components, is positioned inside the device 10. The handle 43, which includes the attachable arms 39, 41 and fulcrum 37, extends outside the device. The contact surfaces of both the thumb and finger components of the NTT face the center wall 19 in direct apposition to the ultraviolet LEDs. The lid 18 of the device is shown in open position. The small arrowheads 14 indicate the direction of removal of the sanitized NTT 30 through the vertical side openings 23, 25 of the sanitizing device. The vertical side exit openings of the sanitizing device are covered by door panels 27, 29, which are hinged to open outward, in the direction of removal of the NTT 30. With reference to FIG. 5, the finger component 33' may have a flat rigid front extension 34 that facilitates sliding the finger component 33' under a flat surface such as a dinner plate. The embodiment of the NTT device 30' in FIG. 5 also includes thumb 31', fingers 33', fulcrum 37', and arms 39', 41'.

Figure 10:
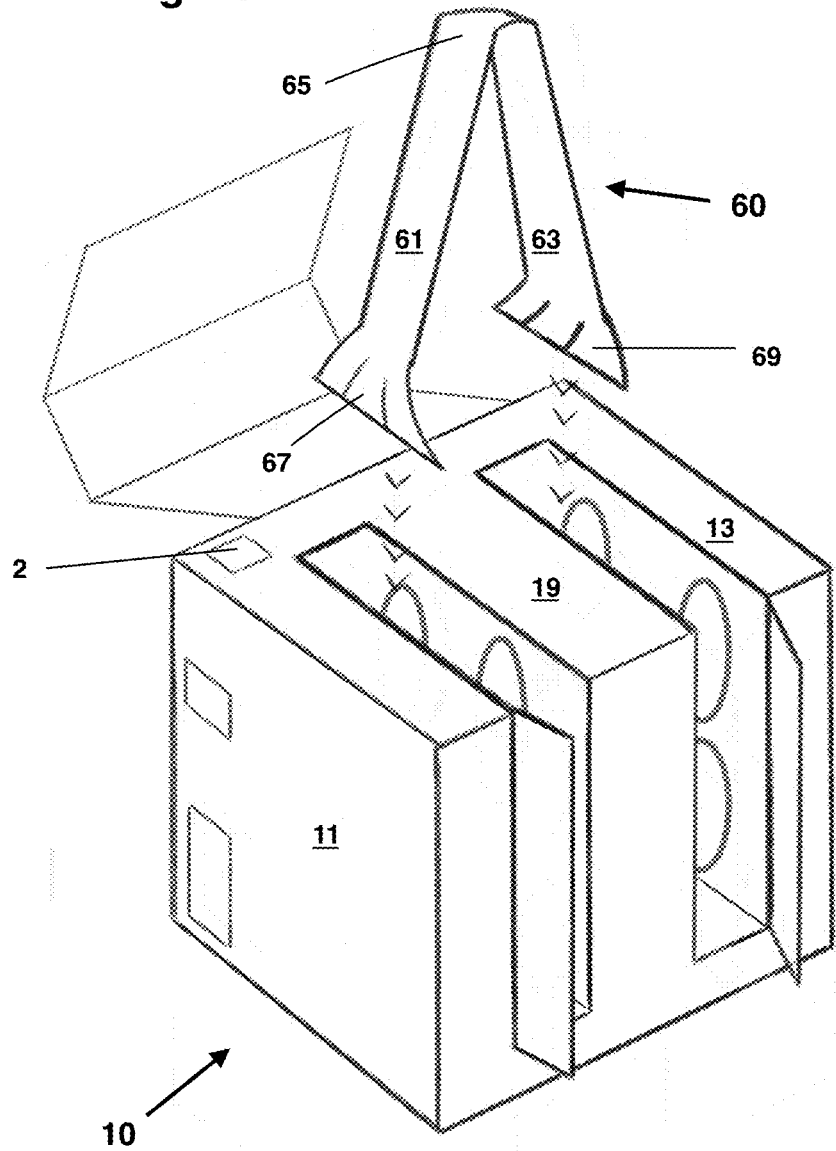
FIG. 10 shows the same side view of the sanitizer of FIGS. 8 and 9 demonstrating insertion of a pair of tongs, as an example of an alternative implement which can be sanitized in the device.
Figure 11:
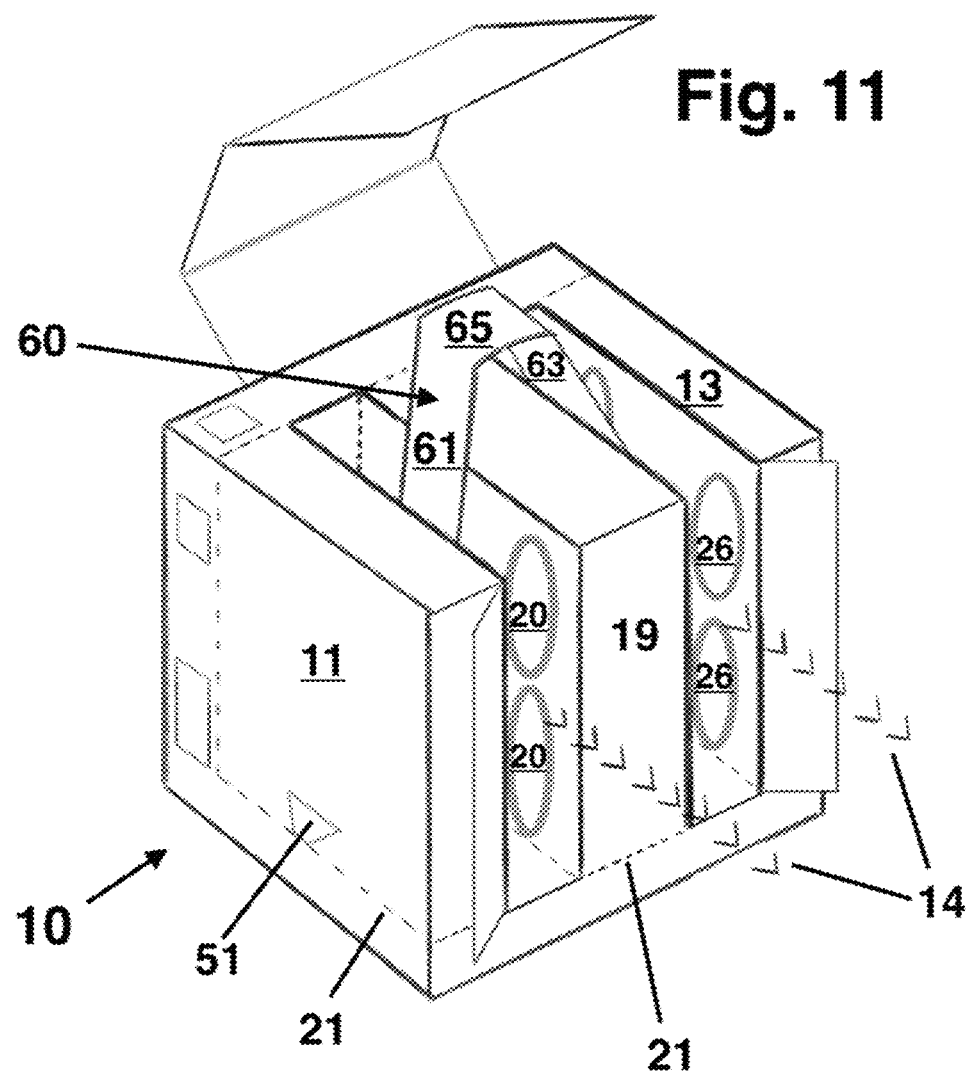
FIG. 11 shows the device of FIGS. 8, 9 and 10 with the pair of tongs fully inserted into the sanitizing device.
Figure 12:
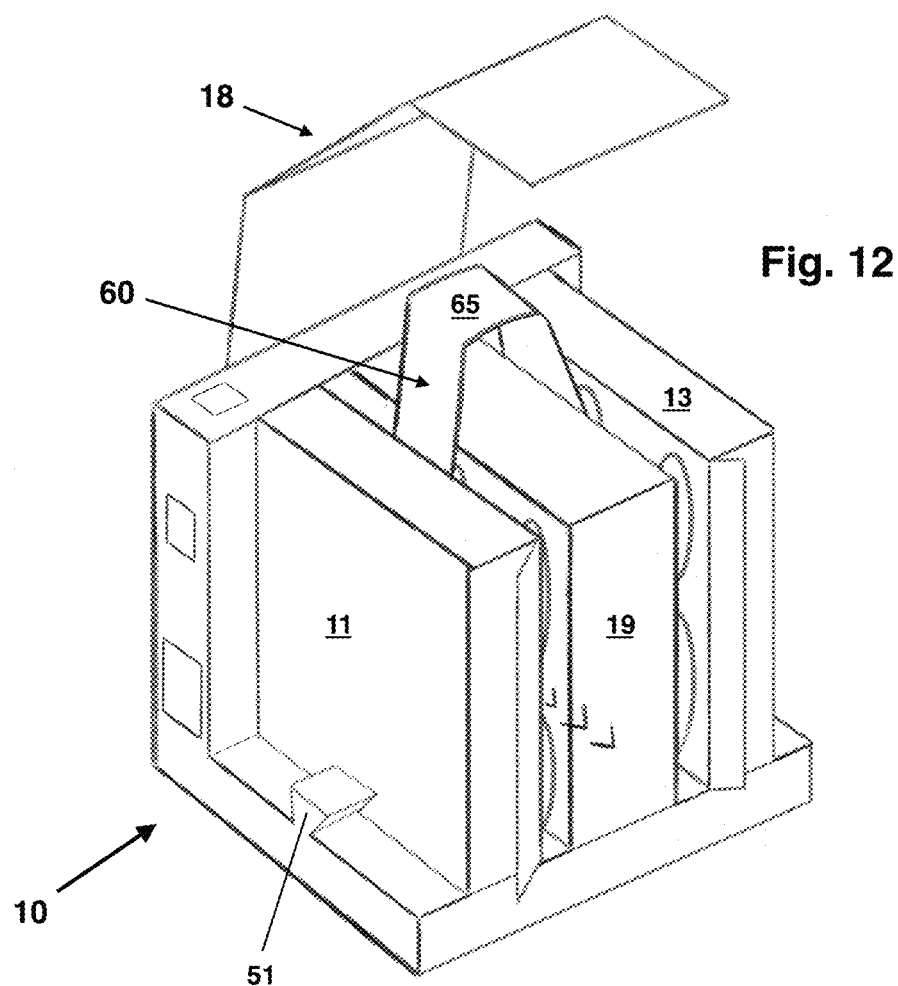
FIG. 12 shows the device of FIGS. 8-11 with the side walls adjusted closer together, enclosing the ultraviolet LEDs tightly around the inserted tongs.

FIG. 9 also highlights the modular, adjustable design of the device. Dotted lines 21 indicate the points of detachment of the individual wall modules and highlight the modular design of the device indicating points of detachment. The trapezoidal shape 12 at the base of the side wall module indicates a guide rail 51 on which the wall 4 slides toward the center wall 19, while remaining attached to the main housing as shown in FIG. 12. The cross-sectional shape of the rail is used to cut-away an exact cross-sectional opening in the wall module, creating a smooth but adherent surface on which the module slides while remaining attached. This is shown in FIG. 12. In some embodiments, other means are utilized for detachment, reattachment and movability of the wall panels. Such means include a clip, snap, adhesive or magnet. FIGS. 10-12 show the device 10 used to sterilize tongs 60, as an example of an alternative implement that may be sanitized using the sanitizing device. The tongs are shown having legs 61, 63 meeting at apex 65 and having enlarged grabbing ends 67, 69. The NTT 30 or 60 can be slid forward through the openings in the chambers 11 and 13 where the doors 27 and 29 are located to remove the NTT after sterilization has been completed.

FIG. 12 shows the device of FIGS. 8-11 with the modular side walls 4, 6 moved together, tightly enclosing the ultraviolet LEDs around the inserted tongs 60. In this embodiment, the side wall modules slide on a guide rail 51. The contact surfaces of the tongs are in optimal position for exposure to the sanitizing ultraviolet light, in direct apposition to the ultraviolet LEDs on the center wall panel.

Figure 13:
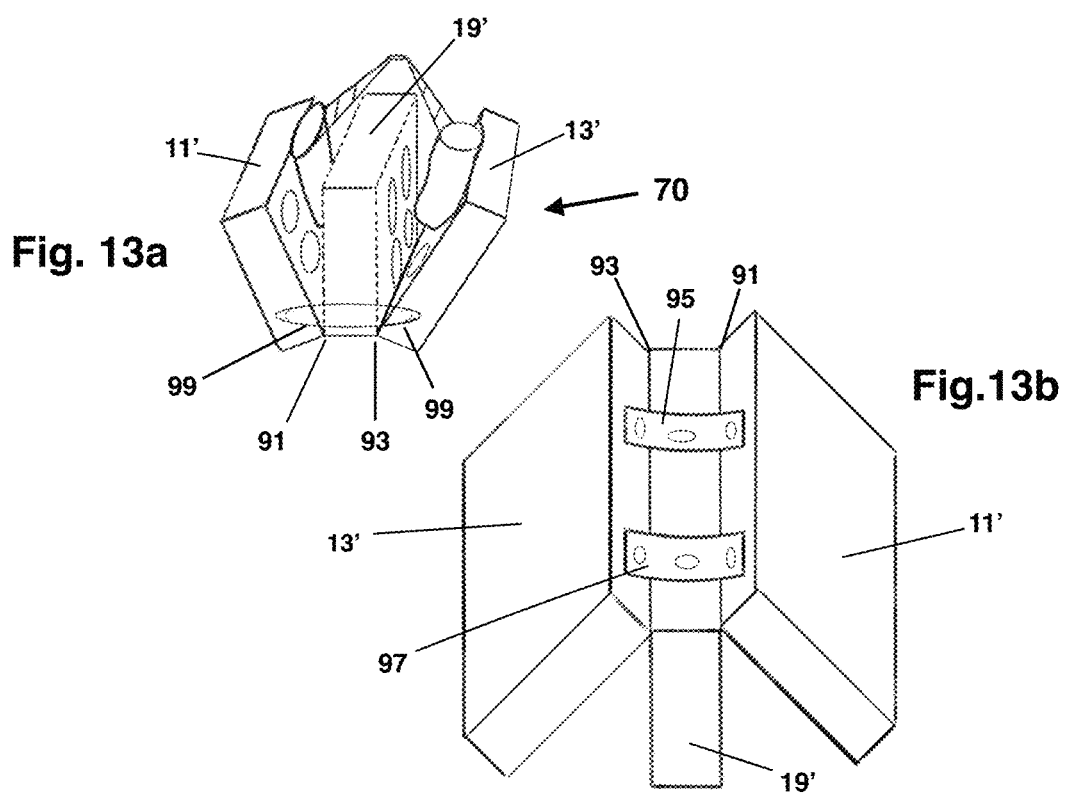
FIGS. 13*a* and 13*b* show an embodiment of the device in which the side wall panels tilt outwards on hinges at completion of sanitization.

FIGS. 13a and 13b show an embodiment 70 of the device in which the side wall panels 4' and 6' tilt outward on hinges 91, 93 at completion of sanitization. The NTT 30 is removed upward in the opposite direction of insertion, preventing recontamination of the NTT. Two different means for restoring the side walls to the upright position are demonstrated. In the upper FIG. 13a, an elastic band mechanism 99 restores the hinged side walls to the vertical position after removal of the NTT. The elastic bands are indicated by the horizontal oval shapes 99 attaching the side walls. In the lower FIG. 13b, flexible panels 95, 97 on the base of the device restore the side walls to the vertical position.

Figure 14:
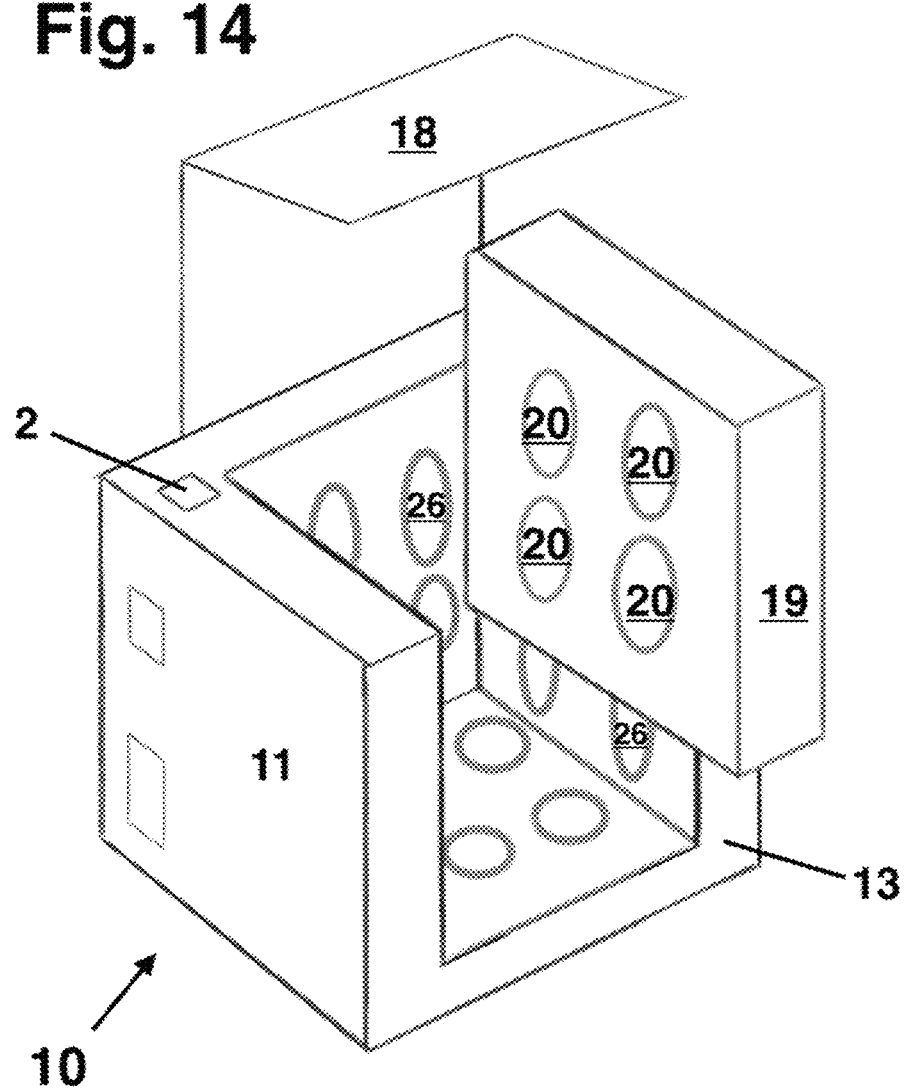
FIG. 14 shows an embodiment of the device with the center panel being removed.

FIG. 14 demonstrates the modular design of the device, showing the center wall 19 being removed. This allows larger objects to be inserted into the device, such as a salt shaker. Removal of the center wall 19 also allows greater access to the interior surfaces of the device for more effective cleaning. This figure also shows the plurality of ultraviolet LEDs 20, 26, designated as oval shapes, throughout the interior and center wall surfaces.

Figure 15:
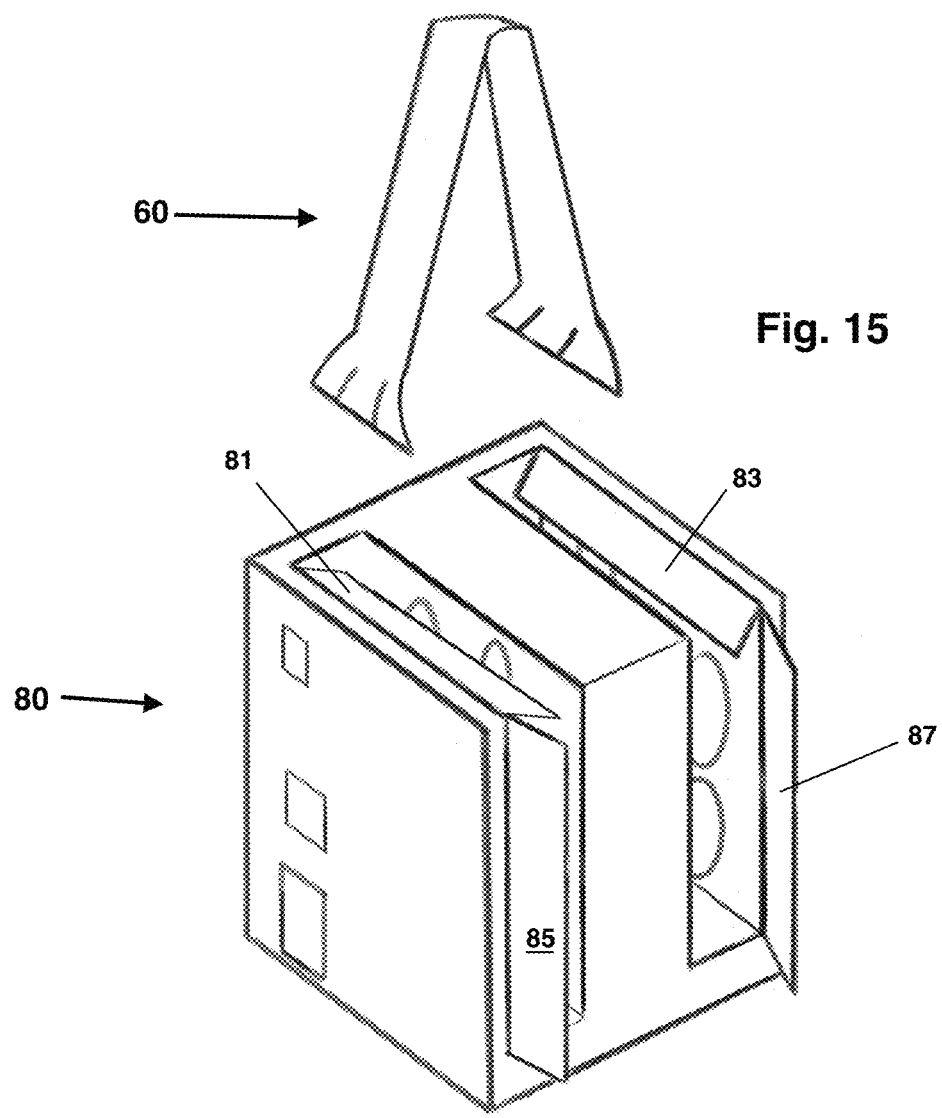
FIG. 15 shows a slightly smaller embodiment of the device, in which the top lid is replaced with individual door panels covering both horizontal insertion openings on top of the device.

FIG. 15 shows a smaller embodiment 80 of the device, with individual door panels 81, 83 on both horizontal top insertion openings and both vertical side exit openings at 85, 87. The horizontal top insertion door panels are hinged to open downward, into the sanitizing device, in the direction of insertion of the NTT. The vertical side exit door panels are hinged to open outwards, in the direction of removal of the NTT.

Figure 6:
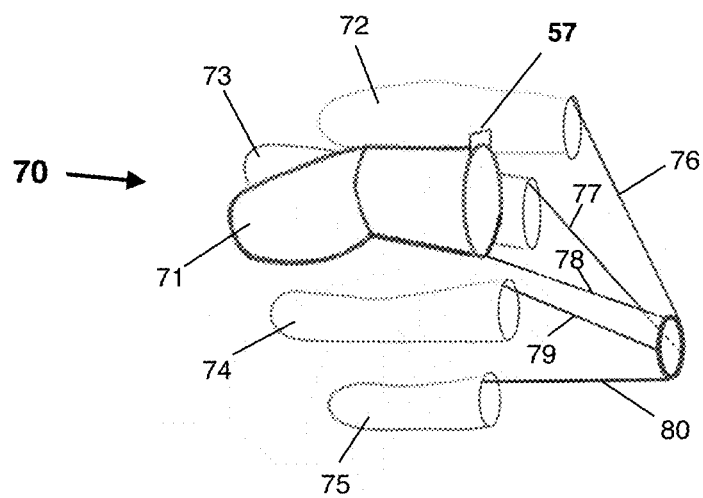
FIG. 6 shows another embodiment of the NTT, with individual finger components, attached to one another.

An alternative embodiment of NTT is shown in FIG. 6 and designated by the reference numeral 70. The NTT 70 has separate receptacles for the thumb 71 and fingers 72, 73, 74, 75. They are interconnected by arms 76, 77, 78, 79 and 80. In another embodiment, the thumb and finger receptacles 71, 72, 73, 74, 75 function completely independently without any connections to each other.

In the embodiment 10 of FIGS. 8-12, the NTT 30 is shown being inserted into the sanitizing device 10, in the direction of the downward facing arrows 15, 17. Any implement used to grasp a dish, glass or other food containing surface, may be inserted, such as the tongs 60 (FIG. 11). Only the contaminated, functional end of the NTT 30 is inserted, which includes the thumb and finger components. The handle of the NTT extends outside the device. The thumb component 31 of the NTT 30 is inserted into the horizontal left top opening 11. The finger component 33 of the NTT 30 is inserted into the horizontal right top opening 13 of the device 10. The thumb and finger components are separated by the center wall 19 of the device as seen in FIG. 9. The contact surfaces of the thumb and finger components of the NTT 30, which are contaminated, face the center wall 19. This orientation places these contaminated contact surfaces in direct apposition to the sanitizing ultraviolet light emitted by the LEDs 20, 26. Once the NTT is inserted, the lid 18 is closed over the top of the device 10 to prevent exposure of ultraviolet light outside of the device. If desired, closure of the lid 18 actuates a spring mechanism (not shown), or other manual means, by which the side wall modules 4, 6 slide together. The side wall modules move along a guide rail 51 (FIG. 12), indicated by the trapezoidal shape at the base of the wall. This action adjustably locates the internal walls of the device, with their embedded ultraviolet LEDs 26 (FIG. 9), against the inserted NTT 30. This process decreases the distance from the contaminated surfaces of the NTT to the surrounding ultraviolet LEDs. Since the intensity of light is exponentially proportional to distance, this novel design optimizes sanitization by maximally shortening this distance. This allows shorter exposure times and lower energy requirements. The ultraviolet LEDs 20, 26 emit light in the wavelengths between 250-300 microns. This range has been shown to sanitize a variety of microbes and is used in many other applications. The virus responsible for the COVID 19 pandemic is particularly sensitive to these wavelengths of ultraviolet light.

With the NTT 30 inserted and the lid closed, the user turns on the device manually with an on/off switch 2 to begin the sanitization cycle. In some embodiments, closure of the top lid automatically turns on the device, using an electric eye or other electro-mechanical means. The constant-current regulator 22 controls operation of the ultraviolet LEDs. In some embodiments, the constant-current regulator 22 is programmable to adjust exposure time, LED intensity and the ultraviolet LED wavelength. These functions of the constant-current regulators are standard features and are readily available from all LED suppliers. The constant-current regulators are frequently provided by manufacturers as integrated components of the LED chip assembly. Different ultraviolet LED wavelengths are provided based on application. The low energy requirement of ultraviolet LEDs allows operation using consumer grade batteries. The invention utilizes either rechargeable or single use, consumer grade batteries.

At completion of the sanitization cycle, which is indicated by an audible or visual indicator, the lid 18 is opened by the user. In some embodiments, this triggers releasing the spring mechanism, sliding the side walls back to the open position along the guide rails. In some embodiments, this may be a manual means. The user then grasps the handle 43 of the NTT 30, which extends outside the device, and slides the NTT out of the vertical side exit openings 23, 25, in the direction of the small arrowheads 14. The vertical side exit openings are covered by door panels 27, 29, which are hinged to open outwards, in the direction of removal of the NTT 30. Removal of the NTT in this direction ensures that the sanitized surfaces of the NTT 30 only come in contact with the interior surfaces of the vertical side exit doors panels, which are at all times sanitary. This novel process avoids recontamination of the now sanitized NTT 30, which may occur if removal proceeded through the horizontal top openings. The horizontal top openings are considered contaminated, since they come in contact with the contaminated NTT during insertion.

The device is a modular design, with the ability to slide, adjust and detach the center and side wall modules. Dotted lines 21 in FIG. 9 around the center and side wall modules of the device indicate detachable edges and the ability disassemble the device. Removal of the wall modules allows more effective cleaning of the device. Removal of the center wall module alone permits larger sized objects to be inserted, such as a salt shaker, for sanitization.

In another embodiment, not shown, the interior walls of the device are lined with a smooth, durable translucent surface, covering the LEDs. This serves to protect the LEDs from breakage during repeated insertion of objects to be sanitized. A smooth surface also improves the ability to clean the interior surfaces of the device. The smooth translucent surface may be made from any material which allows effective transmission of ultraviolet light, such as quartz. In other embodiments, the surface of the interior walls, between the LEDs, is lined with a reflective material to optimize exposure to all surfaces of the inserted implement, which may be irregularly shaped.

In another embodiment, FIG. 15, a lighter, smaller sanitizing device is shown. The side wall modules are thinner. In other embodiments, the center wall panel is thinner as well. The top lid is replaced by door panels 81, 83 covering the horizontal top insertion openings (FIG. 15). These door panels are hinged to open inward, in the direction of insertion of the NTT 30, or other implement such as tongs 60. The hinged door panels prevent removal of the NTT 30, or tongs 60 through the horizontal top openings, since they are hinged to only open in the direction of insertion.

Figure 16:
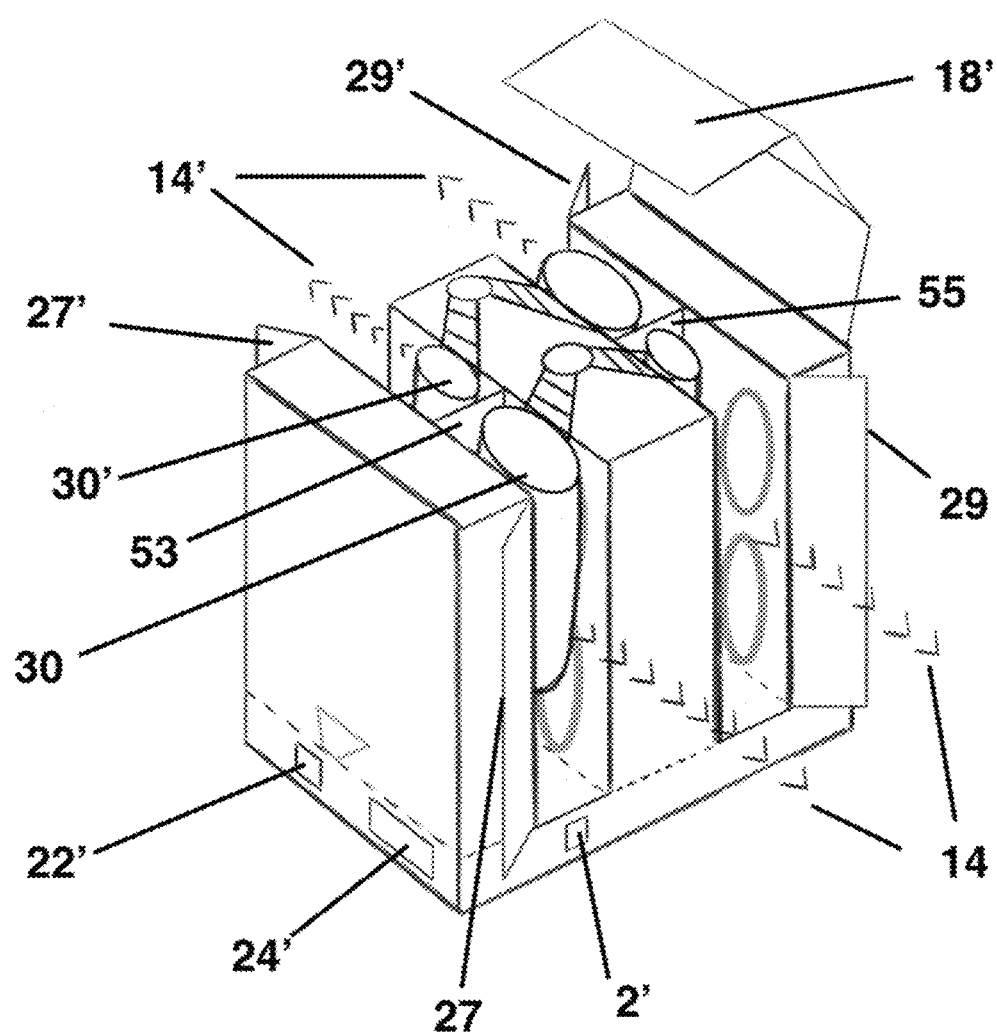
FIG. 16 shows an embodiment treating two NTTs simultaneously, with separate exit openings for each NTT.

In another embodiment, FIG. 16, a sanitizing device treating two NTTs 30, 30' simultaneously is shown. This allows the user to always have a sanitized NTT available while the second NTT is being sanitized. Each NTT has separate exit openings with covered door panels 27, 29, 27', 29'. The interior surface of each door panel remains sanitary due to continuous exposure to the ultraviolet LEDs on the interior of the sanitizing device. The user simply places the contaminated NTT into the device for sanitization, removes their fingers, and inserts them into the second NTT, which has been previously sanitized. The second NTT 30' is then slid out of the second provided exit opening, through the sanitary exit door panels 27', 29'. This process is similar to the embodiments treating a single NTT. Providing separate exit openings for each NTT avoids contamination upon removal of the NTT from the sanitizing device. In this embodiment, the on/off switch 2', battery compartment 24', and constant current regulator 22' are located in the base of the sanitizing device. The two NTTs are separated within the sanitizing device by a partition wall 53, 55 to avoid cross contamination while placing the first contaminated NTT into the device and removing the second sanitized NTT. The lid 18' is mounted on the side wall panel to allow unobstructed removal of either NTT.

While the above description contains many specifics, these should not be construed as limitations on the scope, but rather as an exemplification of several embodiments thereof. Many other variations are possible.

As such, an invention has been disclosed in terms of preferred embodiments thereof, which fulfill each and every one of the objects of the invention as set forth herein above, and provide new and useful ultraviolet LED light sanitizer and devices sanitized thereby of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A device for sanitizing an item, comprising:
   a) a plurality of internal chambers separated by a vertical partition;
   b) a pair of side walls substantially parallel to said vertical partition and located to either side of said vertical partition;
   c) a first of said pair of side walls defining with said vertical partition a first of said plurality of internal chambers;
   d) a second of said pair of side walls defining with said vertical partition a second of said plurality of internal chambers;
   e) said plurality of internal chambers being upwardly open with a top lid movable between a position allowing access to said plurality of internal chambers from above to a position closing access;
   f) said pair of side walls being movable toward and away from said vertical partition to facilitate adjustment of volume of each of said plurality of internal chambers; and
   g) a sources of light within said plurality of internal chambers, said sources of light, when activated, sterilizing objects located within said plurality of internal chambers.

2. The device of claim 1, wherein said sources of light comprises a sources of ultraviolet light.

3. The device of claim 2, wherein said sources of ultraviolet light are located on said vertical partition and on said pair of side walls.

4. The device of claim 2, wherein said sources of ultraviolet light comprise light emitting diodes (LEDs).

5. The device of claim 1, wherein said top lid is pivotable between open and closed positions.

6. The device of claim 1, wherein said sources of light are battery powered.

7. The device of claim 1, wherein said vertical partition is removable.

8. The device of claim 1, wherein each internal chamber includes a forward facing opening.

9. The device of claim 8, wherein each forward facing opening is closeable by a door.

* * * * *